United States Patent [19]

Sakamoto et al.

[11] Patent Number: 4,579,827
[45] Date of Patent: Apr. 1, 1986

[54] MONOCLONAL ANTIBODIES TO HUMAN GASTROINTESTINAL CANCERS AND HYBRIDOMA METHOD OF PRODUCTION OF THE MONOCLONAL ANTIBODIES

[75] Inventors: Junichi Sakamoto; Carlos Cordon-Cardo; Eileen Friedman; Connie L. Finstad, all of New York, N.Y.; Warren E. Enker, Englewood, N.J.; Myron R. Melamed, Scarsdale; Kenneth O. Lloyd, Bronx, both of N.Y.; Herbert F. Oettgen, New Canaan, Conn.; Lloyd J. Old, New York, N.Y.

[73] Assignee: Sloan-Kettering Institute for Cancer Research, N.Y.

[21] Appl. No.: 474,415

[22] Filed: Mar. 11, 1983

[51] Int. Cl.[4] .................. G01N 33/54; C12N 5/00; C12N 15/00
[52] U.S. Cl. .................. 436/536; 436/548; 436/808; 436/813; 260/112 R; 435/4; 435/7; 435/29; 435/68; 435/172.2; 435/240; 435/948; 424/85
[58] Field of Search .......... 436/547, 548, 64, 813, 436/808, 536–542, 815; 435/7, 29, 68, 70, 172, 240, 948, 935, 195, 104, 108, 110, 4, 172.2, 106; 260/112 R; 935/93–111; 424/85

[56] References Cited

U.S. PATENT DOCUMENTS

| | | | |
|---|---|---|---|
| 4,317,877 | 3/1982 | Balis et al. | |
| 4,331,647 | 5/1982 | Goldenberg . | |
| 4,348,376 | 9/1982 | Goldenberg . | |
| 4,349,928 | 9/1982 | Koprowski et al. | 424/1 |
| 4,361,544 | 11/1982 | Goldenberg . | |
| 4,361,549 | 11/1982 | Kung et al. | 424/85 |
| 4,361,550 | 11/1982 | Kung et al. | 424/85 |
| 4,363,799 | 12/1982 | Kung et al. | 424/85 |
| 4,364,932 | 12/1982 | Kung et al. | 424/85 |
| 4,364,933 | 12/1982 | Kung et al. | 424/85 |
| 4,364,934 | 12/1982 | Kung et al. | 424/85 |
| 4,364,935 | 12/1982 | Kung et al. | 424/85 |
| 4,364,936 | 12/1982 | Kung et al. | 424/85 |
| 4,364,937 | 12/1982 | Kung et al. | 424/85 |
| 4,423,147 | 12/1983 | Secher et al. | 435/68 |
| 4,447,538 | 5/1984 | Goodman et al. | 435/253 |

OTHER PUBLICATIONS

Sakamoto, J. et al., AACR Abstracts, p. 225 (3–1983).
Mann, B. D. et al., Federation Proceedings, vol. 41(3), p. 410, #821 (4–1982).
Wahl, R. L. et al., Invest. Radiol., vol. 18(1), pp. 58–62 (1–1983).
Lindholm, L. et al., Int. Arch. Allergy Appl. Immun., vol. 71, pp. 178–181 (1983).
Herlyn, M. et al., J. Clin. Immunology, vol. 2(2), pp. 135–140 (1982).
Brown, A. et al., Bioscience Reports, vol. 3, pp. 163–170 (1983).
Thompson, C. H. et al., British J. Cancer, vol. 47, pp. 595–605 (1983).
Hedin, A. et al., Int. J. Cancer, vol. 30, pp. 547–552 (1982).
Sears, H. F. et al., J. of Surgical Research, vol. 31, pp. 145–150 (1981).
Herlyn, D. M. et al., Int. J. Cancer, vol. 27, pp. 769–774 (1981).
Herlyn, D. et al., Eur. J. Immunology, vol. 9, pp. 657–659 (1979).
Herlyn, D. et al., Cancer Research, vol. 40, pp. 717–721 (1980).
Herlyn, M. et al., Proc. Natl. Acad. Sci., USA, vol. 76, pp. 1438–1442 (1979).
Koprowski, H. et al., Proc. Natl. Acad. Sci., USA, vol. 75, pp. 3405–3409 (1978).
Koprowski, H. et al., Somatic Cell Genetics, vol. 5, pp. 957–972 (1979).
Magnani, J. L. et al., Science, vol. 212, pp. 55–56 (1981).
Steplewski, Z. et al., Cancer Research, vol. 41, pp. 2723–2727 (7–1981).
Stramignoni, D. et al., Int. J. Cancer, vol. 31, pp. 543–552 (1983).
Steplewski, Z. et al., Federation Proceedings, (FASEB), vol. 41(3), p. 726, #2660 (1982).
Magnani, J. L. et al., J. Biol. Chem., vol. 257(23), pp. 14365–14369 (12–1982).
Sears, H. F. et al., Cancer, vol. 49, pp. 1231–1235 (1982).
Farrands, P. A. et al., The Lancet, vol. 2(8295), pp. 397–400 (8–1982).
Dippold, et al. (1980), Proc. Nat'l Acad. Sci. USA 77:6114.
Kohler and Milstein (1975) Nature, 256:495.
Houghton, et al. (1982) J. Exp. Med. 156:1755.
Atkinson, B. F., et al. (1982) Cancer Research 424:4820.
Eisinger, et al. (1982) Proc. Nat'l Acad. Sci. USA 79:2018.
Old, Lloyd J. (1981) Cancer Research 41:361.

Primary Examiner—Thomas G. Wiseman
Assistant Examiner—M. Moskowitz
Attorney, Agent, or Firm—Felfe & Lynch

[57] ABSTRACT

A panel of monoclonal antibodies produced from human gastrointestinal tumors as immunogen is used to diagnose the presence of colon cancer. The antibody panel subsets the human gastrointestinal tract in its reactivity vis-a-vis esophagus, stomach, small intestine and colon. The panel is useful as a diagnostic probe for cancer.

16 Claims, No Drawings

MONOCLONAL ANTIBODIES TO HUMAN GASTROINTESTINAL CANCERS AND HYBRIDOMA METHOD OF PRODUCTION OF THE MONOCLONAL ANTIBODIES

This invention was made in part with government support under Grant No. CA08748 awarded by The National Cancer Institute. The government has certain rights in this invention.

BACKGROUND

This invention concerns monoclonal antibodies recognizing human gastrointestinal (GI) cells. The monoclonal antibodies recognize antigenic markers on normal as well as cancerous GI cells. Capable of distinguishing among normal GI cells as well as colon carcinomas, these mAbs are useful in diagnosis and prognosis of colon and gastrointestinal cancer. Examination of human both wastes, exudates, and fluids with these mAbs is a diagnostic procedure to probe for cancer of the gastrointestinal tract and especially colon cancer. These mAbs are of special importance because of the widespread occurrence of colon cancer.

In 1975 Köhler and Millstein introduced a procedure for the production of monoclonal antibodies (mAbs) using hybrid cells (hybridomas) which allows the production of almost unlimited quantities of antibodies of precise and reproducible specificity. Conventional antisera, produced by immunizing animals with tumor cells or other antigens, contain a myriad of different antibodies differing in their specificity and properties, whereas hybridomas produce a single antibody with uniform characteristics. The Kohler-Millstein procedure entails the fusion of spleen cells from an immunized animal with an immortal myeloma cell line. From the fused cells (hybridomas), clones are selected that produce antibody of the desired specificity. Each clone continues to produce only that one antibody. As hybridoma cells can be cultured indefinitely (or stored frozen in liquid nitrogen), a constant supply of antibody is assured.

Antibodies are proteins that have the ability to combine with and recognize other molecules, known as antigens. Monoclonal antibodies are no different from other antibodies except that they are very uniform in their properties and recognize only one antigen or a portion of an antigen known as a determinant.

In the case of cells, the determinant recognized is an antigen on or in the cell which reacts with the antibody. It is through these cell antigens that a particular antibody recognizes, i.e. reacts with, a particular kind of cell. Thus the cell antigens are markers by which the cell is identified.

These antigenic markers may be used to observe the normal process of cell differentiation and to locate abnormalities within a given cell system. The process of differentiation is accompanied by changes in the cell surface antigenic phenotype, and antigens that distinguish cells belonging to distinct differentiation lineages or distinguish cells at different phases in the same differentiation lineage may be observed if the correct antibody is available. Initial recognition of differentiation antigens came about through analysis of surface antigens of T-cell leukemias of the mouse and the description of the TL, Thy-1, and Lyt series of antigens. (Old, Lloyd J., Cancer Research, 41, 361–375, February 1981) The analysis of these T-cell differentiation antigens was greatly simplified by the availability of normal T cells and B cells of mouse and man and is relatively advanced. (See U.S. Pat. Nos. 4,361,549–550; 4,364,932–37 and 4,363,799 concerning mAb to Human T-cell antigens). Little is known about differentiation antigens displayed on normal and neoplastic cells belonging to other lineages.

This is due to the difficulty of obtaining a ready source of the appropriate normal cell type as well as the vagaries of the art of monoclonal antibodies. The preparation of hybrid cell lines can be successful or not depending on such experimental factors as nature of the innoculant, cell growth conditions, hybridization conditions etc. Thus it is not always possible to predict successful hybridoma preparation of one cell line although success may have been achieved with another cell line.

Progress in defining surface antigens on melanocytes was made possible by the recently discovered technique of culturing melanocytes from normal skin (Eisinger, et al., Proc. Nat'l. Acad. Sci. USA, 79 2018 (March 1982). This method provides a renewable source of proliferating cells for the analysis of melanocyte differentiation antigens. Likewise, a large number of cell lines derived from melanomas have now been established and these have facilitated the analysis of melanoma surface antigens. The advent of mAbs has greatly accelerated knowledge about the surface antigens of malignant melanoma. Cell markers on both melanomas and melanocytes have been identified. A panel of typing monoclonal antibodies has been selected which recognizes differentiation antigen characteristics at each stage of development in both melanocytes and melanomas. These differentiation antigens may be used to classify melanocytes and melanomas and to group them into characteristic sub-sets. Dippold et al. *Proc. Nat'l. Acad. Sci. U.S.A.* 77, 6114 (1980) and Houghton, et al. *J. Exp. Med.* 156, 1755 (1982). Immunoassay of melanocytes and melanoma cells within sub-sets is thus made possible.

SUMMARY

Cancers of the gastrointestinal tract are especially widespread; stomach cancer in Japan, colon cancer in the west and U.S.A. Early diagnosis would be desireable to prevent drastic surgery and loss of life. Clearly positive diagnosis help to support the surgical decision. Cytohistological methods to date are not always successful. A panel group of twelve mAbs of the present invention recognizing cancerous colon cells enables such a distinction for the first time. In addition, the panel distinguishes normal from cancerous cells.

The invention thus comprises hybridoma cell lines producing mAbs recognizing human colon cancer cells, from the group of CLH6, CLT85, CLT479, CLT174, CLH68, CLT152, CLH70, HT29/15, HT29/26, HT29/36, CLT218, CLT15, CLT307 and CLT86. These mAbs of the invention recognize colon glycoprotein (gp) antigens molecular weights 25 kd, 29 kd and 95 kd (mAbs CLH70, HT29/26 and CLT479 respectively). mAb CLT152 recognizes a protein antigen of 52 kd. The antigens for CLH6, CLT85, CLT174 and HT29/36 are heat stable and therefore probably glycolipids. CLT85, CLT479, CLT174, HT29/36, CLH68, CLT152 and HT29/15 are gamma sub one ($\gamma_1$) immunoglobulins. HT29/26 is a gamma sub 2A ($\gamma_{2A}$) immunoglobulin. HT29/36 is a gamma sub 3 ($\gamma_3$) immunoglobulin and CLT218, CLT307, CLT86 and CLH6 are mu ($\mu$) immunoglobulins. (HT 29/36 is the same mAb as HT 29-36 HT 29/15 is the same mAb as HT 29-15 and HT 29/26 is the same mAb as HT 29-26).

DESCRIPTION

A preferred embodiment of the present invention is to test a human speciman as for example human body wastes, fluids and exudates with each of the monoclonal antibodies of the panel. The cells are tested or contacted separately with each of the monoclonal antibodies in a series of dilutions. Thus, an assay for cancer is possible with minimal patent disruption. Indeed, the present invention permits testing of human urine specimans for cell fragments containing antigenic markers for the monoclonal antibodies. Entire cells need not be present. Cytohistological methods requiring whole cells are not always successful.

The monoclonal antibodies of the present invention were prepared by an improved Kohler-Millstein procedure wherein spleen cells from a mouse (or other mammal) immunized with human cancerous colon cells from established human tumor cell lines were fused with mouse myeloma to form hybridomas. By serological screening, antibodies from these hybridomas were found which recognize differentiation antigens on normal bladder and/or cancerous bladder. Other tissues, both normal and cancerous, may be recognized as well by some of these monoclonal antibodies. A system of classification of normal as well as cancerous colon based on these differentiation antigens is now possible, and serological assays for tumors of the colon have been developed. These assays are of special use in the early diagnosis of gastrointestinal cancer especially colon cancer.

The assay of the present invention comprises contacting a tissue containing colon cells with the antibody recognizing colon cell antigens, preferably monoclonal antibodies to one or more cell antigens of the gastrointestinal antigenic system, and observing the immunoserological or immunopathological antigenic reaction between said monoclonal antibody and said antigen. In a preferred embodiment of the invention, the tissue sample to be contacted is gastrointestinal tissue and the antigenic reaction of the contacted tissue is observed by well known techniques such as immunofluorescence, Rosette formation with sheep or human red blood cells linked to Protein A or anti-Ig direct absorption and the like. In another embodiment of the present invention, the tissue to be assayed is first excised and is then either freshly, or after being frozen or embedded in paraffin by methods well-known in the art, contacted with the monoclonal antibodies of the invention. Observation of the reaction is as before.

In another preferred embodiment of the present invention, the tissue to be assayed comprises the intact body of an individual or a whole portion thereof. The antibody, tagged with a radioactive or other energy-producing element, is administered to the individual, and the whole body or part thereof is scanned externally for localization of radioactivity at the site of cancerous gastrointestinal cells. In another preferred embodiment cancerous colon cells are located.

The present invention also makes possible the treatment of gastrointestinal tumors in a patient wherein the monoclonal antibody recognizing the cell antigen of cancerous colon or other cancerous GI cells, is administered to the patient in an amount effective to inhibit the growth or proliferation of cancer cells. In a preferred embodiment of this method, the antibody is tagged with a potentially tissue destructive agent which causes destruction of the cancer cells. Examples of tissue destructive agents comprise chemotoxic agents, chemotherapeutic agents including vaccines, radionuclides, toxins, complement activators, clotting activators and the like.

The above examples are for illustrative purposes only and are not meant to limit the scope of the invention.

EXAMPLES OF ANTIBODIES, AND ANTIGENS RECOGNIZED

The following examples are intended to illustrate the invention without limiting same in any manner especially with respect to substantially functional equivalents of hybridomas, monoclonal antibodies and cell lines described and claimed herein which equivalents can be produced in accordance with the invention following the procedures outlined in the specification of this application.

The monoclonal antibodies selected for use in the present invention were derived from spleen cells of mice immunized with whole cells of colon carcinoma cell lines such as Tallevi and HT-29 by fusion methods well known in the art.

A group of monoclonal antibodies which were found to recognize specific cell antigens of gastrointestinal cells, was selected as the grastrointestinal panel. This panel and the antigenic systems recognized are given in Tables I & II. Heterogeneity of human colon carcinoma is therein noted. The table data point out and define the heterogeneity of colon carcinomas. Gastrointestinal antigenic systems are defined by these mAbs as determined by serological analysis with over 70 tumor cell lines; 18 colon cancers, over 50 non-gastrointestinal cancers as well as immunopathology on frozen sections of normal adult and normal fetal tissue. (See Table I & II)

Several of the antigens, as defined by the monoclonal antibodies of the panel, are expressed differentially by cell populations within the adult GI system. CLT152 antigen is expressed by epithelial cells of the GI mucosa of esophagus, stomach, small intestine and colon, but is not found in other adult tissues. CLH70, CLT307, CLT86 and CLH68 antigens are expressed by adult stomach, small intestine and colon. CLT218 is expressed by adult small intestine and colon. HT29/26 is expressed by colon and some cells of small intestine in the adult. CLT15 also is expressed by normal colon epithelium as well as some upper GI cells except stomach in adult tissues. Thus the mAbs antigens HT29/26, CLT15, CLT218, CLH70, CLT307, CLT86 and CLH68 occur in adult colon epithelial cells; they vary among themselves in their pattern of distribution within the rest of the GI tract. There is some limited expression of these antigens in epithelial cells of other tissues as well See Table II. Thus, for example, CLT218, CLT86, HT29/26 antigens are expressed on bronchial epithelium whereas CLH6, HT29/36 and HT29/15 are not. Thus, the panel antibodies differ in their expression on normal cells even as to similar cells of other tissues.

It is important that the mAbs CLH6, CLT85, and 29/36 do not react with normal adult tissue in immunopathology of frozen tissue sections but do react with distinct subsets of colon adenocarcenomas.

Serologically CLT85 reacts with approximately 11 of 17 colon cancer lines, and CLH6 with approximately 8 out of 17 colon cancer cell lines. CLT85 and CLH6 show no reaction with normal adult cells in serology.

Thus normal versus neoplastic cells of the colon can be differentiated and assayed by contacting a speciman from a human patient with each of the 14 monoclonal antibodies of the panel in serial dilution, and observing any antigen antibody reaction by any of the methods cited. Although 14 hybridomas producing monoclonal antibody against gastrointestinal cell antigens are presented, it is obvious that the present invention encompasses all the mAbs exhibiting the characteristics described therein, especially the embodiment describing reaction with normal as well as tumor cell antigens of the GI tract.

Changes in cell antigens are associated with different stages of differentiation and different stages of cancer. Thus this invention technique defined cell antigens associated with differentiation and cancer of the GI tract.

The following hybridoma cell lines are maintained on deposit at Sloan-Kettering Institute, 1275 York Avenue, New York, NY 10021 under designations corresponding to the mAb produced by each hybridoma as follows:

CLH 6, CLT 85, CLT 479, CLT 174, CLH 68, CLT 152, CLH 70, HT 29/15, HT 29/26, HT 29/36, CLT 218, CLT 15, CLT 307 and CLT 86.

Said hybridoma cell lines have been deposited on Mar. 11, 1983 with the American Type Culture Collection, 1230 Parklawn Drive, Rockville, Md. 20852 under ATCC designations corresponding to the above Sloan-Kettering designations as follows:

| Sloan-Kettering deposit # | Corresponding ATCC deposit accession # |
|---|---|
| CLH 6 | HB 8232 |
| CLT 85 | HB 8240 |
| CLT 479 | HB 8241 |
| CLT 174 | HB 8242 |
| CLT 68 | HB 8243 |
| CLT 152 | HB 8244 |
| CLH 70 | HB 8245 |
| HT 29/15 | HB 8246 |
| HT 29/26 | HB 8247 |
| HT 29/36 | HB 8248 |
| CLT 218 | HB 8249 |
| CLT 15 | HB 8250 |
| CLT 307 | HB 8251 |
| CLT 86 | HB 8252 |

LEGEND TO TABLE I

Serological reaction of colon panel monoclonal antibodies with human tumor cell lines of various tissues by rosette formation with human red blood cells conjugated with rabbit anti-Ig, Dippold Supra
where
 0 = no reaction by rosette formation or absorption
 2 = positive rosette reaction <1,000 fold dilution antibody supernatant
 3 = positive rosette reaction at >1,000 fold dilution antibody supernatant
 1 = positive reaction by absorption test only.
If there is no rosette reaction, the absorption test was done. Thus if a mAb was negative for the rosette reaction but absorbed onto the test antigen system it was deemed to be a positive reaction such that
 1 = positive reaction by the absorption test though mAb gives a negative test for rosette formation i.e. 0 test for rosette reaction is further tested by the absorption test. Therefore 0 on this table indicates no reaction by either absorption or rosette reactions. For comparison, mAb 19.9 was obtained from H. Kaprowski and assayed as well alongside the mAbs of the present invention Atkinson, B. F. et al., Cancer Research, 42:4820–4823(1982).
In Table I actual titers are included.
Immunogen for CLT series is Tallevi, for HT and CLH antibodies the immunogen is HT-29.

LEGEND TO TABLE II

Immunopathological reaction of colon panel monoclonal antibodies with fetal and adult normal human tissue in frozen section by indirect immunofluorescence.
 0 = no reaction
 + = positive reaction
 ± = heterogeneous reaction within the tissue
For comparison, mAb 19.9 was obtained from H. Kaprowski and assayed as well alongside the mAbs of the present invention Atkinson, B. F. et al., Cancer Research, 42:4820–4823(1982).

TABLE I
Serology
Serological Reaction of Monoclonal Antibodies
Produced from Human Colon Tumor Immunogen With Various
Human Cancer Cell Lines
IMMUNIZING TUMOR: COLON

| Antibody | CLH 6 | CLT 85 | CLT 479 | CLT 174 | CLH 68 | CLT 152 | CLH 70 | HT29 −15 | HT29 −26 | HT29 −36 | CLT 218 | CLT 15 | CLT 307 | CLT 86 | 19.9 |
|---|---|---|---|---|---|---|---|---|---|---|---|---|---|---|---|
| IG class of antibody: | μ | γ1 | γ1 | γ1 | γ1 | γ1 | | γ1 | γ2a | γ3 | μ | μ | μ | μ | |
| gp Antigen detected | | | gp95 | | | p52 | gp25 | | gp29 | | | | | | |
| CELLS TESTED | | | | | | | | | | | | | | | |
| Colon Ca.: | | | | | | | | | | | | | | | |
| HT 29 | 3 | 3 | 3 | 3 | 3 | 3 | 3 | 3 | 3 | 3 | 0 | 0 | 3 | 3 | $10^3$ |
| SW 48 | 3 | 3 | 2 | 3 | 0 | 3 | 0 | 0 | 3 | 3 | 2 | 2 | 0 | 0 | $10^3$ |
| SW 403 | 0 | 3 | 3 | 3 | 2 | 3 | 0 | 3 | 3 | 2 | 3 | 0 | 3 | 3 | $10^6$ |
| SW 480 | 3 | 3 | 3 | 3 | 3 | 3 | 3 | 3 | 3 | | 3 | 3 | 3 | 3 | 10 |
| SW 620 | 3 | 3 | 2 | 0 | 0 | 3 | 3 | 3 | 3 | 3 | 2 | 3 | 2 | 0 | $10^2$ |
| SW 837 | 0 | 0 | 0 | 1 | 0 | 0 | 0 | 0 | 3 | | 2 | 0 | 0 | 0 | 0 |
| SW 1083 | 2 | 0 | 0 | 0 | 0 | 0 | 0 | 0 | 3 | 0 | 3 | 0 | 0 | 0 | 0 |
| SW 1116 | 0 | 1 | 3 | 3 | 3 | 3 | 0 | 3 | 3 | 3 | 3 | 0 | 3 | 3 | $10^2$ |
| SW 1222 | 0 | 3 | 3 | 3 | 3 | 3 | 3 | 3 | 3 | 3 | 0 | 0 | 3 | 3 | $10^3$ |
| SW 1417 | 1 | 1 | 3 | 3 | 3 | 3 | 3 | 3 | 3 | | 0 | 0 | 2 | 3 | 0 |
| CACO2 | 2 | 3 | 0 | 0 | 0 | 2 | 3 | 3 | 3 | 0 | 3 | 0 | 0 | 0 | 0 |
| SK-CO-1 | 0 | 0 | 0 | 0 | 0 | 0 | 2 | 3 | 3 | | 0 | 0 | 0 | 0 | 0 |
| Tallevi | 0 | 3 | 3 | 3 | 3 | 3 | 3 | 3 | 3 | 0 | 3 | 3 | 3 | 0 | $10^3$ |

TABLE I-continued

Serology
Serological Reaction of Monoclonal Antibodies
Produced from Human Colon Tumor Immunogen With Various
Human Cancer Cell Lines
IMMUNIZING TUMOR: COLON

| Antibody | CLH 6 | CLT 85 | CLT 479 | CLT 174 | CLH 68 | CLT 152 | CLH 70 | HT29 −15 | HT29 −26 | HT29 −36 | CLT 218 | CLT 15 | CLT 307 | CLT 86 | 19.9 |
|---|---|---|---|---|---|---|---|---|---|---|---|---|---|---|---|
| Moutsiatzos | 1 | 0 | 0 | 0 | 0 | 0 | 0 | 0 | 0 | 0 | 0 | 0 | 0 | | 0 |
| Kolraga | 0 | 3 | 3 | 3 | 3 | 3 | 3 | 3 | 3 | | 3 | 2 | 0 | 3 | 10 |
| Friedland | 0 | 0 | 0 | 3 | 3 | 2 | 3 | 0 | 3 | 0 | 3 | 0 | 3 | 0 | 0 |
| Redmond | 1 | 0 | 0 | 0 | 0 | 0 | 0 | 3 | 3 | 0 | 2 | 0 | 0 | 0 | 1 |
| HSO7O3T | | | | | | | | | | | | | | | |
| Pancreas Ca.: | | | | | | | | | | | | | | | |
| CAPAN 1 | 3 | 0 | 0 | 1 | 0 | 0 | 3 | 0 | | | 0 | 0 | 3 | 0 | 0 |
| CAPAN 2 | 0 | 3 | 3 | 3 | 3 | 3 | 0 | 3 | | | 3 | 3 | 0 | 3 | $10^2$ |
| SW 850 | 0 | 0 | 0 | 0 | 0 | 0 | 0 | 0 | | | 0 | 0 | 0 | 0 | |
| SW 979 | 0 | 0 | 0 | 0 | 0 | 0 | 0 | 0 | | | 0 | 0 | | | |
| Liver Ca.: | | | | | | | | | | | | | | | |
| SK-HEP-1 | 1 | 0 | 0 | 0 | 0 | 0 | 2 | 3 | 3 | 0 | 0 | 0 | 0 | 0 | 0 |
| Biliary duct: | | | | | | | | | | | | | | | |
| Charles | 0 | 0 | 2 | 0 | 0 | 0 | 0 | 3 | 3 | | 0 | 0 | | 0 | 0 |
| Astrocytoma: | | | | | | | | | | | | | | | |
| Goodstein | 0 | 0 | 0 | 0 | 0 | 0 | 0 | 0 | | | 0 | 0 | 0 | 0 | 0 |
| U251 | 0 | 0 | 0 | 0 | 0 | 0 | 0 | 0 | | | 0 | 0 | 0 | | 0 |
| Becker | 0 | 0 | 0 | 0 | 0 | 0 | 0 | 0 | | | 0 | 0 | 0 | | 0 |
| Machino | 0 | 0 | 0 | 0 | 0 | 0 | 0 | 0 | 0 | 0 | 0 | 0 | 0 | 0 | 0 |
| Jones | 0 | 0 | 0 | 0 | 0 | 0 | 0 | 0 | | | 0 | 0 | 0 | | 0 |
| AJ | 0 | 0 | 0 | 0 | 0 | 0 | 0 | 0 | 0 | | 0 | 0 | 0 | | 0 |
| Lear | 0 | 0 | 0 | 0 | 0 | 0 | 0 | 0 | 0 | 0 | 0 | 0 | 0 | 0 | 0 |
| Healy | 0 | 0 | 0 | 0 | 0 | 0 | 0 | 0 | 0 | | 0 | 0 | 0 | 0 | 0 |
| T98 | 0 | 0 | 0 | 0 | 0 | 0 | 0 | 0 | | | 0 | 0 | 0 | 0 | 0 |
| U373 | 0 | 0 | 0 | 0 | 0 | 0 | 0 | 0 | 0 | 0 | 0 | 0 | 0 | 0 | 0 |
| Melanoma: | | | | | | | | | | | | | | | |
| SK-MEL-31(3) | 0 | 0 | 0 | 0 | 0 | 0 | | 2 | 0 | 0 | 0 | 0 | 0 | 0 | 0 |
| -23 | 0 | 0 | 0 | 0 | 0 | 0 | 0 | 0 | 0 | | 0 | 0 | 0 | 0 | 0 |
| -13 | 0 | 0 | 0 | 0 | 0 | 0 | 0 | 0 | | 0 | 0 | 0 | 0 | 0 | 0 |
| -37 | 0 | 0 | 0 | 0 | 0 | 0 | 0 | 2 | 0 | 0 | 0 | 0 | 0 | 0 | 0 |
| -93(2) | 0 | 0 | 0 | 0 | 3 | 0 | 0 | 3 | 2 | 0 | 0 | 0 | 0 | 0 | 0 |
| -28 | 0 | 0 | 0 | 0 | 0 | 0 | 0 | 0 | 0 | 3 | 0 | 0 | 0 | 0 | 0 |
| MeWo | 0 | 0 | 0 | 0 | 0 | 0 | 0 | 0 | 0 | 0 | 0 | 0 | 0 | 0 | 0 |
| Neuroblastoma: | | | | | | | | | | | | | | | |
| SK-N-MC | 0 | 0 | 0 | 0 | 0 | 0 | 3 | 0 | 0 | 0 | 0 | 0 | 0 | 0 | 0 |
| -SH | 0 | 0 | 0 | 0 | 0 | 0 | 3 | 0 | 0 | 0 | 0 | 0 | 0 | 0 | 0 |
| -BE2 | 0 | 0 | 0 | 0 | 0 | 0 | 3 | 0 | 0 | 0 | 0 | 0 | 0 | 0 | 0 |
| LAN-1-5 | 0 | 0 | 0 | 0 | 0 | 0 | 0 | 0 | 0 | 0 | 0 | 0 | 0 | 0 | 0 |
| CHP-234N | | | | | | | | | | | | | | | |
| Breast Ca.: | | | | | | | | | | | | | | | |
| MDA MB 361 | 0 | 0 | 0 | 0 | 0 | 0 | 3 | 3 | 0 | 0 | 0 | 0 | 0 | 0 | 0 |
| MDA MB 231 | 0 | 0 | 0 | 0 | 0 | 0 | 2 | 3 | 3 | 0 | 0 | 0 | 3 | 0 | 0 |
| BT 20 | 0 | 0 | 0 | 0 | 0 | 0 | 0 | 3 | 3 | 0 | 0 | 0 | 0 | 0 | 0 |
| CAMA | 0 | 0 | 1 | 1 | 0 | 0 | 0 | 3 | 0 | | 3 | 3 | 3 | 3 | 0 |
| SK-BR-3 | 0 | 0 | 0 | 0 | 0 | 0 | 0 | 3 | 0 | | 0 | 0 | 0 | 0 | 0 |
| ALAb | 0 | 0 | 0 | 0 | 0 | 0 | 3 | 3 | | | 0 | 0 | 0 | 0 | 0 |
| MCF-7 | 0 | 0 | 0 | 0 | 0 | 0 | 0 | 3 | 3 | 3 | 3 | 0 | 0 | 3 | 0 |
| Kidney Ca: | | | | | | | | | | | | | | | |
| SK-RC-6 | 0 | 0 | 0 | 0 | 0 | 0 | 0 | 0 | 3 | 0 | 0 | 0 | 0 | 0 | |
| -7 | 0 | 0 | 0 | 0 | 0 | 0 | 0 | 0 | 3 | 0 | | | | | 0 |
| -29 | 0 | 0 | 0 | 0 | 0 | 3 | 0 | 0 | 3 | 0 | 0 | 0 | 0 | | 0 |
| -4 | 0 | 0 | 0 | 0 | 0 | 0 | 0 | 0 | 3 | 0 | 0 | 0 | 0 | | |
| Ovary Ca: | | | | | | | | | | | | | | | |
| SK-OV-3 | 0 | 0 | 0 | 0 | 0 | 0 | 0 | 0 | 3 | 0 | 0 | 0 | 0 | 0 | 0 |
| ROAC | 0 | 0 | 0 | 0 | 0 | 0 | 3 | 0 | 3 | | 0 | 0 | 0 | 0 | 0 |
| 2774 | 0 | 0 | 0 | 0 | 0 | 0 | 0 | 0 | 3 | | 0 | 0 | 0 | 0 | 0 |
| SW 626 | 0 | 0 | 3 | 3 | 0 | 0 | 0 | 3 | 3 | | 3 | 0 | 3 | 3 | 0 |
| Shustak | 0 | 0 | 0 | 0 | 0 | 3 | 0 | 3 | 3 | | 3 | 3 | 3 | 3 | 0 |
| Turanek | 0 | | 2 | 0 | 0 | 3 | 2 | 3 | 3 | 0 | 0 | 0 | 0 | 3 | 10 |
| Uterine Ca: | | | | | | | | | | | | | | | |
| ME180 | 0 | 0 | 0 | 0 | 0 | 0 | 0 | 0 | 3 | 3 | 0 | 0 | 0 | 0 | 0 |
| Chorioepithelium: | | | | | | | | | | | | | | | |
| SVCC | 0 | 0 | 2 | | 0 | 0 | 0 | 0 | 3 | | 0 | 0 | 3 | 0 | 0 |
| Lung Ca: | | | | | | | | | | | | | | | |
| SK-LC-3 | 0 | 0 | 2 | 0 | 0 | 0 | 3 | 3 | 3 | 0 | 0 | 0 | 0 | 0 | 0 |
| -4 | 0 | 0 | 0 | 0 | 0 | 0 | 0 | 3 | 3 | 2 | 0 | 0 | 0 | 0 | 10 |
| -5 | 1 | 0 | 0 | 0 | 0 | 0 | 0 | 3 | 3 | 0 | 0 | 0 | 0 | 0 | 0 |
| -6 | 0 | 0 | 0 | 0 | 0 | 0 | 3 | 2 | 0 | 0 | 0 | 0 | 2 | 0 | 0 |
| -7 | 0 | 0 | 0 | 0 | 0 | 0 | 0 | 0 | 3 | 2 | 0 | 0 | 0 | 0 | 0 |
| -8 | 0 | 0 | 0 | 2 | 0 | 0 | 0 | 0 | 3 | 3 | 0 | 0 | 0 | 0 | 0 |
| -13 | 0 | 0 | 0 | 0 | 0 | 0 | 2 | 0 | 3 | 2 | 0 | 0 | 0 | 0 | 0 |
| Lawson | 0 | 1 | 1 | 1 | 0 | 3 | 2 | 3 | 3 | 2 | 3 | 0 | 0 | 3 | $10^3$ |

TABLE I-continued

Serology
Serological Reaction of Monoclonal Antibodies
Produced from Human Colon Tumor Immunogen With Various
Human Cancer Cell Lines
IMMUNIZING TUMOR: COLON

| Antibody | CLH 6 | CLT 85 | CLT 479 | CLT 174 | CLH 68 | CLT 152 | CLH 70 | HT29 −15 | HT29 −26 | HT29 −36 | CLT 218 | CLT 15 | CLT 307 | CLT 86 | 19.9 |
|---|---|---|---|---|---|---|---|---|---|---|---|---|---|---|---|
| Bladder Ca: | | | | | | | | | | | | | | | |
| T-24 | 0 | 0 | 0 | 0 | 0 | 0 | 0 | 0 | 0 | 3 | 0 | 0 | 0 | 0 | 0 |
| TCC SUP | 0 | 0 | 0 | 0 | 0 | 0 | 0 | 0 | 0 | 0 | 0 | 0 | 0 | 0 | 0 |
| 253J | 0 | 0 | 0 | 0 | 0 | 0 | 0 | 0 | 0 | 0 | 0 | 3 | 0 | 0 | 0 |
| 639V | 0 | 0 | 0 | 0 | 0 | 0 | 0 | 0 | 3 | 3 | 0 | 0 | 0 | 0 | 0 |
| 486P | 0 | 0 | 0 | 0 | 0 | 0 | 3 | 3 | 3 | 0 | 0 | 0 | 0 | 0 | 0 |

TABLE II

Immunopathology
Normal Tissue Distribution of the Monoclonal
Antibodies Produced from Human
Colon Tumor Immunogen

| | CLT 85 | 28 | CLH 6 | HT 29/36 | HT 29/15 | CLT 479 | CLT 15 | CLT 174 | CLT 86 | CLH 70 | CLT 152 | 19.9 | CLT 307 | CLT 218 | HT 29/26 | CLH 68 |
|---|---|---|---|---|---|---|---|---|---|---|---|---|---|---|---|---|
| A. FETAL TISSUES | | | | | | | | | | | | | | | | |
| LUNG | ± | | 0 | 0 | 0 | + | + | + | + | + | + | | + | + | + | 0 |
| Bronchial Epithelium | ± | | 0 | 0 | 0 | ± | ± | ± | + | + | + | | + | + | + | 0 |
| Cartilage | 0 | | 0 | 0 | 0 | 0 | 0 | 0 | 0 | 0 | 0 | | 0 | 0 | 0 | 0 |
| Pneumocytes | 0 | | 0 | 0 | 0 | 0 | 0 | 0 | 0 | 0 | 0 | | 0 | 0 | 0 | 0 |
| Connect. Tis | 0 | | 0 | 0 | 0 | 0 | 0 | 0 | 0 | 0 | 0 | 0 | 0 | 0 | 0 | 0 |
| HEART | 0 | | 0 | 0 | 0 | 0 | 0 | 0 | 0 | 0 | 0 | 0 | 0 | 0 | 0 | 0 |
| THYMUS | 0 | | 0 | 0 | 0 | + | 0 | 0 | 0 | 0 | + | + | 0 | 0 | 0 | + |
| Hassal's C. | 0 | | 0 | 0 | 0 | + | 0 | 0 | 0 | 0 | + | + | 0 | 0 | 0 | + |
| Thymocytes | 0 | | 0 | 0 | 0 | 0 | 0 | 0 | 0 | 0 | 0 | 0 | 0 | 0 | 0 | 0 |
| SPLEEN | 0 | | 0 | 0 | 0 | 0 | 0 | 0 | 0 | 0 | 0 | 0 | 0 | 0 | 0 | 0 |
| White Pulp | 0 | | 0 | 0 | 0 | 0 | 0 | 0 | 0 | 0 | 0 | 0 | 0 | 0 | 0 | 0 |
| Red Pulp | 0 | | 0 | 0 | 0 | 0 | 0 | 0 | 0 | 0 | 0 | 0 | 0 | 0 | 0 | 0 |
| LIVER | 0 | | 0 | 0 | 0 | 0 | 0 | 0 | + | + | + | 0 | + | + | + | + |
| Hepatocytes | 0 | | 0 | 0 | 0 | 0 | 0 | 0 | 0 | 0 | 0 | 0 | 0 | 0 | 0 | 0 |
| Biliary Epi Cells | 0 | | 0 | 0 | 0 | 0 | 0 | 0 | + | + | + | 0 | + | + | + | + |
| GALLBLAD. | 0 | | 0 | 0 | 0 | 0 | 0 | 0 | + | + | + | 0 | + | + | + | + |
| ESOPHAGUS | 0 | | 0 | 0 | 0 | ± | 0 | ± | ± | 0 | ± | ± | + | ± | ± | ± |
| STOMACH | 0 | ± | 0 | 0 | 0 | 0 | 0 | ± | + | ± | ± | ± | + | 0 | ± |
| SMALL INT. | 0 | | 0 | 0 | 0 | 0 | 0 | 0 | 0 | 0 | 0 | 0 | 0 | 0 | ± | + |
| COLON | ± | ± | 0 | 0 | ± | ± | ± | + | + | + | ± | + | + | + | + |
| PANCREAS | 0 | + | 0 | + | + | + | + | + | + | + | + | + | + | + | + | 0 |
| Exocrine | 0 | ± | 0 | + | + | + | + | + | + | + | + | + | + | + | + | 0 |
| Endocrine | 0 | 0 | 0 | 0 | 0 | 0 | 0 | 0 | 0 | 0 | 0 | 0 | 0 | 0 | 0 |
| KIDNEY | 0 | + | 0 | 0 | 0 | 0 | 0 | + | + | 0 | 0 | 0 | + | + | 0 |
| Glomerulus | 0 | 0 | 0 | 0 | 0 | 0 | 0 | 0 | 0 | 0 | 0 | 0 | 0 | 0 | 0 |
| Prox. Tub. | 0 | 0 | 0 | 0 | 0 | 0 | 0 | 0 | + | 0 | 0 | 0 | 0 | 0 | 0 |
| Distal Tub. | 0 | + | 0 | 0 | 0 | 0 | 0 | + | 0 | 0 | 0 | 0 | + | + | 0 |
| Collec. Tub | 0 | + | 0 | 0 | 0 | 0 | 0 | + | 0 | 0 | 0 | 0 | + | + | 0 |
| URETER | 0 | + | 0 | ± | 0 | 0 | 0 | ± | 0 | + | 0 | + | + | + | + |
| UR. BLAD. | 0 | + | 0 | ± | 0 | 0 | 0 | ± | 0 | + | 0 | + | + | + | + |
| ADRENAL | 0 | 0 | 0 | 0 | 0 | 0 | 0 | 0 | 0 | 0 | 0 | 0 | 0 | 0 | 0 |
| Cortex | 0 | 0 | 0 | 0 | 0 | 0 | 0 | 0 | 0 | 0 | 0 | 0 | 0 | 0 | 0 |
| Medulla | 0 | 0 | 0 | 0 | 0 | 0 | 0 | 0 | 0 | 0 | 0 | 0 | 0 | 0 | 0 |
| TESTES | 0 | 0 | 0 | 0 | 0 | 0 | 0 | 0 | 0 | 0 | 0 | 0 | 0 | 0 | 0 |
| Germ. Cells | 0 | 0 | 0 | 0 | 0 | 0 | 0 | 0 | 0 | 0 | 0 | 0 | 0 | 0 | 0 |
| Endoc. Cel. | 0 | 0 | 0 | 0 | 0 | 0 | 0 | 0 | 0 | 0 | 0 | 0 | 0 | 0 | 0 |
| Connect. T. | 0 | 0 | 0 | 0 | 0 | 0 | 0 | 0 | 0 | 0 | 0 | 0 | 0 | 0 | 0 |
| OVARY | 0 | 0 | 0 | 0 | 0 | 0 | 0 | 0 | 0 | 0 | 0 | 0 | 0 | 0 | 0 |
| Germ. Cells | 0 | 0 | 0 | 0 | 0 | 0 | 0 | 0 | 0 | 0 | 0 | 0 | 0 | 0 | 0 |
| Connect. T. | 0 | 0 | 0 | 0 | 0 | 0 | 0 | 0 | 0 | 0 | 0 | 0 | 0 | 0 | 0 |
| FALLOP. T. | 0 | 0 | 0 | 0 | 0 | 0 | 0 | 0 | 0 | 0 | 0 | 0 | 0 | + | 0 |
| UTERUS | 0 | 0 | 0 | 0 | 0 | 0 | 0 | + | + | 0 | 0 | 0 | + | + | 0 |
| Endometrium | 0 | 0 | 0 | 0 | 0 | 0 | 0 | + | + | 0 | 0 | 0 | + | + | 0 |
| Myometrium | 0 | 0 | 0 | 0 | 0 | 0 | 0 | 0 | 0 | 0 | 0 | 0 | 0 | 0 | 0 |
| CERVIX | 0 | 0 | 0 | 0 | 0 | 0 | 0 | + | 0 | 0 | 0 | 0 | + | + | + |
| Endocervix | 0 | 0 | 0 | 0 | 0 | 0 | 0 | + | 0 | 0 | 0 | 0 | + | + | 0 |
| Exocervix | 0 | 0 | 0 | 0 | 0 | 0 | 0 | ± | 0 | 0 | 0 | 0 | 0 | 0 | + |
| SKIN | 0 | 0 | 0 | 0 | 0 | ± | 0 | + | 0 | + | 0 | + | + | + | + |
| Epidermis | 0 | 0 | 0 | 0 | 0 | ± | 0 | ± | 0 | ± | 0 | ± | ± | ± | ± |
| Melanocytes | 0 | 0 | 0 | 0 | 0 | 0 | 0 | 0 | 0 | 0 | 0 | 0 | 0 | 0 | 0 |
| Sweat Gland | 0 | 0 | 0 | 0 | 0 | 0 | 0 | 0 | 0 | 0 | 0 | 0 | 0 | 0 | 0 |
| Sebac. Gld. | 0 | 0 | 0 | 0 | 0 | 0 | 0 | 0 | 0 | 0 | 0 | 0 | 0 | + | 0 |
| Hair Fol. | 0 | 0 | 0 | 0 | 0 | 0 | 0 | 0 | 0 | 0 | 0 | 0 | 0 | 0 | 0 |
| Dermis C.T. | 0 | 0 | 0 | 0 | 0 | 0 | 0 | 0 | 0 | 0 | 0 | 0 | 0 | 0 | 0 |

TABLE II-continued

Immunopathology
Normal Tissue Distribution of the Monoclonal
Antibodies Produced from Human
Colon Tumor Immunogen

| | CLT 85 | 28 | CLH 6 | HT 29/36 | HT 29/15 | CLT 479 | CLT 15 | CLT 174 | CLT 86 | CLH 70 | CLT 152 | 19.9 | CLT 307 | CLT 218 | HT 29/26 | CLH 68 |
|---|---|---|---|---|---|---|---|---|---|---|---|---|---|---|---|---|
| BRAIN | 0 | 0 | 0 | 0 | 0 | 0 | 0 | 0 | 0 | 0 | 0 | 0 | 0 | 0 | 0 | 0 |
| Neurons | 0 | 0 | 0 | 0 | 0 | 0 | 0 | 0 | 0 | 0 | 0 | 0 | 0 | 0 | 0 | 0 |
| Glial Cells | 0 | 0 | 0 | 0 | 0 | 0 | 0 | 0 | 0 | 0 | 0 | 0 | 0 | 0 | 0 | 0 |
| Dendrites | 0 | 0 | 0 | 0 | 0 | 0 | 0 | 0 | 0 | 0 | 0 | 0 | 0 | 0 | 0 | 0 |
| LYMPH NODE | 0 | 0 | 0 | 0 | 0 | 0 | 0 | 0 | 0 | 0 | 0 | 0 | 0 | 0 | 0 | 0 |
| BLOOD VES. | 0 | 0 | 0 | 0 | 0 | 0 | 0 | 0 | 0 | 0 | 0 | 0 | 0 | 0 | 0 | 0 |
| Endoth. Cel. | 0 | 0 | 0 | 0 | 0 | 0 | 0 | 0 | 0 | 0 | 0 | 0 | 0 | 0 | 0 | 0 |
| Smooth Ms. | 0 | 0 | 0 | 0 | 0 | 0 | 0 | 0 | 0 | 0 | 0 | 0 | 0 | 0 | 0 | 0 |
| SOFT TIS. | 0 | 0 | 0 | 0 | 0 | 0 | 0 | 0 | 0 | 0 | 0 | 0 | 0 | 0 | 0 | 0 |
| SECRETION | ± | 0 | 0 | 0 | 0 | + | 0 | + | + | + | + | + | + | + | + | + |
| B. ADULT TISSUES | | | | | | | | | | | | | | | | |
| LUNG | 0 | 0 | 0 | 0 | 0 | 0 | 0 | 0 | + | 0 | 0 | + | 0 | + | + | 0 |
| Bronchial | 0 | 0 | 0 | 0 | 0 | 0 | 0 | 0 | ± | 0 | 0 | ± | 0 | + | + | 0 |
| Epithelium | | | | | | | | | | | | | | | | |
| Cartilage | 0 | 0 | 0 | 0 | 0 | 0 | 0 | 0 | 0 | 0 | 0 | 0 | 0 | 0 | 0 | 0 |
| Glandular | 0 | 0 | 0 | 0 | 0 | 0 | 0 | 0 | + | 0 | 0 | + | 0 | + | + | 0 |
| Epithelium | | | | | | | | | | | | | | | | |
| Pneumocytes | 0 | 0 | 0 | 0 | 0 | 0 | 0 | 0 | 0 | 0 | 0 | 0 | 0 | 0 | 0 | 0 |
| Connect. Tis | 0 | 0 | 0 | 0 | 0 | 0 | 0 | 0 | 0 | 0 | 0 | 0 | 0 | 0 | 0 | 0 |
| HEART (ms) | 0 | 0 | 0 | 0 | 0 | 0 | 0 | 0 | 0 | 0 | 0 | 0 | 0 | 0 | 0 | 0 |
| SPLEEN | 0 | 0 | 0 | 0 | 0 | 0 | 0 | 0 | 0 | 0 | 0 | 0 | 0 | 0 | 0 | 0 |
| White pulp | 0 | 0 | 0 | 0 | 0 | 0 | 0 | 0 | 0 | 0 | 0 | 0 | 0 | 0 | 0 | 0 |
| Red pulp | 0 | 0 | 0 | 0 | 0 | 0 | 0 | 0 | 0 | 0 | 0 | 0 | 0 | 0 | 0 | 0 |
| LIVER | 0 | 0 | 0 | 0 | 0 | 0 | 0 | + | 0 | + | + | + | + | + | + | 0 |
| Hepatocyte | 0 | 0 | 0 | 0 | 0 | 0 | 0 | 0 | 0 | 0 | 0 | 0 | 0 | ± | 0 | 0 |
| Bil. Epit. | 0 | 0 | 0 | 0 | 0 | 0 | 0 | + | 0 | + | + | + | + | + | + | 0 |
| Sinusoids | 0 | 0 | 0 | 0 | 0 | 0 | 0 | 0 | 0 | 0 | 0 | 0 | 0 | 0 | 0 | 0 |
| GALLBLADDER | 0 | 0 | 0 | 0 | 0 | 0 | 0 | + | 0 | + | + | + | + | + | + | 0 |
| ESOPHAGUS | 0 | 0 | 0 | 0 | 0 | 0 | + | ± | 0 | 0 | + | ± | + | + | 0 | 0 |
| STOMACH | 0 | 0 | 0 | 0 | 0 | 0 | 0 | 0 | ± | 0 | + | + | ± | 0 | 0 | + |
| SM. INTEST. | 0 | 0 | 0 | 0 | 0 | 0 | ± | 0 | + | ± | + | 0 | + | ± | 0 | + |
| COLON | 0 | 0 | 0 | 0 | 0 | 0 | + | 0 | + | + | + | 0 | + | + | + | + |
| G.I. Smc | 0 | 0 | 0 | 0 | 0 | 0 | 0 | 0 | 0 | 0 | 0 | 0 | 0 | 0 | 0 | 0 |
| PANCREAS | 0 | 0 | 0 | 0 | + | + | + | + | + | + | + | + | + | + | + | 0 |
| Exocrine | 0 | 0 | 0 | 0 | + | + | + | + | + | + | + | + | + | + | + | 0 |
| Endocrine | 0 | 0 | 0 | 0 | 0 | 0 | 0 | 0 | 0 | 0 | 0 | 0 | 0 | 0 | 0 | 0 |
| KIDNEY | 0 | 0 | 0 | 0 | 0 | 0 | 0 | 0 | 0 | 0 | + | 0 | 0 | 0 | + | 0 |
| Glomerulus | 0 | 0 | 0 | 0 | 0 | 0 | 0 | 0 | 0 | 0 | 0 | 0 | 0 | 0 | 0 | 0 |
| Prox. Tub. | 0 | 0 | 0 | 0 | 0 | 0 | 0 | 0 | 0 | 0 | 0 | 0 | 0 | 0 | 0 | 0 |
| Henle's L. | 0 | 0 | 0 | 0 | 0 | 0 | 0 | 0 | 0 | 0 | 0 | 0 | 0 | 0 | ± | 0 |
| Distal Tub. | 0 | 0 | 0 | 0 | 0 | 0 | 0 | 0 | 0 | 0 | + | 0 | 0 | 0 | + | 0 |
| Collec. Tub | 0 | 0 | 0 | 0 | 0 | 0 | 0 | 0 | + | 0 | + | 0 | 0 | 0 | + | 0 |
| URETER | 0 | 0 | 0 | 0 | 0 | 0 | 0 | ± | 0 | 0 | 0 | 0 | + | + | + | + |
| URI. BLAD. | 0 | 0 | 0 | 0 | 0 | 0 | 0 | ± | 0 | 0 | 0 | 0 | + | + | + | + |
| ADRENAL | 0 | 0 | 0 | 0 | 0 | 0 | 0 | 0 | 0 | 0 | 0 | 0 | 0 | 0 | 0 | 0 |
| Cortex | 0 | 0 | 0 | 0 | 0 | 0 | 0 | 0 | 0 | 0 | 0 | 0 | 0 | 0 | 0 | 0 |
| Medulla | 0 | 0 | 0 | 0 | 0 | 0 | 0 | 0 | 0 | 0 | 0 | 0 | 0 | 0 | 0 | 0 |
| THYROID | 0 | 0 | 0 | 0 | 0 | 0 | 0 | 0 | 0 | 0 | 0 | 0 | 0 | 0 | 0 | 0 |
| Epithelium | 0 | 0 | 0 | 0 | 0 | 0 | 0 | 0 | 0 | 0 | 0 | 0 | 0 | 0 | 0 | 0 |
| Colloid | 0 | 0 | 0 | 0 | 0 | 0 | 0 | 0 | 0 | 0 | 0 | 0 | + | + | + | + |
| BREAST | 0 | 0 | 0 | 0 | + | 0 | 0 | + | 0 | 0 | + | + | + | + | + | + |
| Duct Cells | 0 | 0 | 0 | 0 | + | 0 | 0 | + | + | 0 | + | + | ± | + | + | 0 |
| Acinar Cel. | 0 | 0 | 0 | 0 | + | 0 | 0 | 0 | 0 | 0 | + | ± | 0 | 0 | 0 | 0 |
| Connec. Tis. | 0 | 0 | 0 | 0 | 0 | 0 | 0 | 0 | + | 0 | 0 | 0 | 0 | + | + | + |
| PROSTATE | 0 | 0 | 0 | 0 | 0 | 0 | 0 | 0 | 0 | + | 0 | + | 0 | + | + | + |
| Epithelium | 0 | 0 | 0 | 0 | 0 | 0 | 0 | 0 | 0 | + | 0 | + | 0 | 0 | 0 | 0 |
| Stroma | 0 | 0 | 0 | 0 | 0 | 0 | 0 | 0 | 0 | 0 | 0 | 0 | 0 | 0 | 0 | 0 |
| TESTES | 0 | 0 | 0 | 0 | 0 | 0 | 0 | 0 | 0 | 0 | 0 | 0 | 0 | 0 | 0 | 0 |
| Germ Cells | 0 | 0 | 0 | 0 | 0 | 0 | 0 | 0 | 0 | 0 | 0 | 0 | 0 | 0 | 0 | 0 |
| Endocrine Cel | 0 | 0 | 0 | 0 | 0 | 0 | 0 | 0 | 0 | 0 | 0 | 0 | 0 | 0 | 0 | 0 |
| Connec. Tis. | 0 | 0 | 0 | 0 | 0 | 0 | 0 | 0 | 0 | 0 | 0 | 0 | 0 | 0 | 0 | 0 |
| OVARY | 0 | 0 | 0 | 0 | 0 | 0 | 0 | 0 | 0 | 0 | 0 | 0 | 0 | 0 | 0 | 0 |
| Germ Cells | 0 | 0 | 0 | 0 | 0 | 0 | 0 | 0 | 0 | 0 | 0 | 0 | 0 | 0 | 0 | 0 |
| Connec. Tis. | 0 | 0 | 0 | 0 | 0 | 0 | 0 | 0 | 0 | 0 | 0 | 0 | 0 | 0 | 0 | 0 |
| FALLOP. TUB. | 0 | 0 | 0 | 0 | 0 | 0 | 0 | 0 | 0 | 0 | 0 | 0 | 0 | 0 | + | 0 |
| UTERUS | 0 | 0 | 0 | 0 | 0 | 0 | 0 | 0 | 0 | 0 | 0 | 0 | 0 | 0 | + | 0 |
| Endometrium | 0 | 0 | 0 | 0 | 0 | 0 | 0 | 0 | 0 | 0 | 0 | 0 | 0 | 0 | 0 | 0 |
| Myometrium | 0 | 0 | 0 | 0 | 0 | 0 | 0 | 0 | 0 | 0 | 0 | 0 | 0 | 0 | + | + |
| CERVIX | 0 | 0 | 0 | 0 | 0 | 0 | 0 | 0 | 0 | + | 0 | + | 0 | 0 | + | 0 |
| Endocervix | 0 | 0 | 0 | 0 | 0 | 0 | 0 | 0 | 0 | + | 0 | + | 0 | 0 | + | + |
| Exocervix | 0 | 0 | 0 | 0 | 0 | 0 | 0 | 0 | 0 | 0 | 0 | 0 | 0 | 0 | 0 | 0 |
| PLACENTA | 0 | 0 | 0 | 0 | 0 | 0 | 0 | 0 | 0 | 0 | 0 | 0 | 0 | 0 | 0 | 0 |
| Cytotrophb. | 0 | 0 | 0 | 0 | 0 | 0 | 0 | 0 | 0 | 0 | 0 | 0 | 0 | 0 | 0 | 0 |
| Syncytotrb. | 0 | 0 | 0 | 0 | 0 | 0 | 0 | 0 | 0 | 0 | 0 | 0 | 0 | 0 | 0 | 0 |
| Sinusoids | 0 | 0 | 0 | 0 | 0 | 0 | 0 | 0 | 0 | 0 | 0 | 0 | + | + | 0 | 0 |

TABLE II-continued

Immunopathology
Normal Tissue Distribution of the Monoclonal
Antibodies Produced from Human
Colon Tumor Immunogen

| | CLT 85 | CLH 28 | CLH 6 | HT 29/36 | HT 29/15 | CLT 479 | CLT 15 | CLT 174 | CLT 86 | CLH 70 | CLT 152 | 19.9 | CLT 307 | CLT 218 | HT 29/26 | CLH 68 |
|---|---|---|---|---|---|---|---|---|---|---|---|---|---|---|---|---|
| SKIN | 0 | 0 | 0 | 0 | + | ± | 0 | ± | ± | + | + | 0 | 0 | 0 | ± | 0 |
| Epidermis | 0 | 0 | 0 | 0 | 0 | 0 | 0 | 0 | 0 | 0 | 0 | 0 | 0 | + | + | 0 |
| Melanocytes | 0 | 0 | 0 | 0 | 0 | 0 | 0 | 0 | 0 | 0 | 0 | 0 | 0 | ± | ± | 0 |
| Sweat Gld. | 0 | 0 | ± | 0 | + | ± | 0 | ± | + | + | + | 0 | 0 | 0 | 0 | 0 |
| Sebaceous G. | 0 | 0 | 0 | 0 | + | 0 | 0 | 0 | 0 | + | 0 | 0 | 0 | 0 | 0 | 0 |
| Dermis CT | 0 | 0 | 0 | 0 | 0 | 0 | 0 | 0 | 0 | 0 | 0 | 0 | 0 | 0 | 0 | 0 |
| BRAIN | 0 | 0 | 0 | 0 | 0 | 0 | 0 | 0 | 0 | 0 | 0 | 0 | 0 | 0 | 0 | 0 |
| Neurons | 0 | 0 | 0 | 0 | 0 | 0 | 0 | 0 | 0 | 0 | 0 | 0 | 0 | 0 | 0 | 0 |
| Glial Cell | 0 | 0 | 0 | 0 | 0 | 0 | 0 | 0 | 0 | 0 | 0 | 0 | 0 | 0 | 0 | 0 |
| Dendrites | 0 | 0 | 0 | 0 | 0 | 0 | 0 | 0 | 0 | 0 | 0 | 0 | 0 | 0 | 0 | 0 |
| LYMPH NODE | 0 | 0 | 0 | 0 | 0 | 0 | 0 | 0 | 0 | 0 | 0 | 0 | 0 | 0 | 0 | 0 |
| Fol/Modul | 0 | 0 | 0 | 0 | 0 | 0 | 0 | 0 | 0 | 0 | 0 | 0 | 0 | 0 | 0 | 0 |
| BLOOD VES. | 0 | 0 | 0 | 0 | 0 | 0 | 0 | 0 | 0 | 0 | 0 | 0 | 0 | 0 | 0 | 0 |
| Endothelium | 0 | 0 | 0 | 0 | 0 | 0 | 0 | 0 | 0 | 0 | 0 | 0 | 0 | 0 | 0 | 0 |
| Smooth Ms. | 0 | 0 | 0 | 0 | 0 | 0 | 0 | 0 | 0 | 0 | 0 | 0 | 0 | 0 | 0 | 0 |
| CAPILLARIES | 0 | 0 | 0 | 0 | 0 | 0 | 0 | 0 | 0 | 0 | 0 | 0 | 0 | 0 | 0 | 0 |
| SKELETAL MS | 0 | 0 | 0 | 0 | 0 | 0 | 0 | 0 | 0 | 0 | 0 | 0 | 0 | 0 | 0 | 0 |
| SOFT TISSUE | 0 | 0 | 0 | 0 | 0 | 0 | 0 | 0 | 0 | 0 | 0 | 0 | 0 | 0 | 0 | 0 |
| SECRETIONS | 0 | 0 | ± | + | + | + | + | + | + | + | + | + | + | + | + | + |

What is claimed is:

1. Monoclonal antibody characterized by immunological binding to human gastrointestinal cell antigens wherein said monoclonal antibody is selected from the group consisting of human gastrointestinal-cell-antigen-binding monoclonal antibodies CLH6 (HB 8232), CLT85 (HB8240), CLT479 (HB8241), CLT174 (HB8242), CLH68 (HB8243), CLT152 (HB8244), CLH70 (HB8245), HT29/15 (HB8246), HT29/26 (HB8247), HT29/36 (HB8248), CLT218 (HB8249), CLT15 (HB8250), CLT307 (HB8251), and CLT86 (HB8252).

2. Monoclonal antibody of claim 1 characterized by immunological binding to human gastrointestinal antigens said antigens being selected from the group consisting of glycoprotein antigen, glycolipid antigen and protein antigen.

3. Monoclonal antibody of claim 2 wherein the gastrointestinal glycoprotein antigens have molecular weights in the range of approximately 25-95 kd.

4. Monoclonal antibody of claim 3 wherein the gastrointestinal glycoprotein antigens are selected from the group consisting of 25 kd glycoprotein antigen, 29 kd glycoprotein antigen and 95 kd glycoprotein antigen.

5. Monoclonal antibody of claim 2 wherein the molecular weight of the gastrointestinal protein antigen is a 52 kd protein.

6. Panel of monoclonal antibodies for the diagnosis of human gastrointestinal cancer wherein the panel consists of two or more different monoclonal antibodies selected from the group consisting of human gastrointestinal-cell-antigen-binding monoclonal antibodies CLH6 (HB 8232), CLT85 (HB8240), CLT479 (HB8241), CLT174 (HB8242), CLH68 (HB8243), CLT152 (HB8244), CLH70 (HB8245), HT29/15 (HB8246), HT29/26 (HB8247), HT29/36 (HB8248), CLT218 (HB8249), CLT15 (HB8250), CLT307 (HB8251), and CLT86 (HB8252).

7. Monoclonal-antibody-producing-hybridoma cell lines characterized by the production of monoclonal antibody which monoclonal antibody is characterized by immunological binding to human gastrointestinal cell antigen and wherein said monoclonal antibody is selected from the group consisting of human gastrointestinal-cell-antigen-binding monoclonal antibodies CLH6 (HB8232), CLT85 (HB8240), CLT479 (HB8241), CLT174 (HB8242), CLH68 (HB8243), CLT152 (HB8244), CLH70 (HB8245), HT29/15 (HB8246), HT29/26 (HB8247), HT29/36 (HB8248), CLT218 (HB8249), CLT15 (HB8250), CLT307 (HB8251), and CLT86 (HB8252).

8. Monoclonal-antibody-producing-hybridoma cell lines formed by fusing a myeloma cell line and spleen cells derived from a mammal immunized with established culture cell lines of human gastrointestinal cell carcinomas wherein the monoclonal antibody produced is selected from the group consisting of human gastrointestinal-cell-antigen-binding monoclonal antibodies CLH6 (HB 8232), CLT85 (HB8240), CLT479 (HB8241), CLT174 (HB8242), CLH68 (HB8243), CLT152 (HB8244), CLH70 (HB8245), HT29/15 (HB8246), HT29/26 (HB8247), HT29/36 (HB8248), CLT218 (HB8249), CLT15 (HB8250), CLT307 (HB8251), and CLT86 (HB8252).

9. Method for differentiating between normal and abnormal human gastrointestinal cells which comprises contacting a human gastrointestinal specimen containing gastrointestinal cellular material with a panel of two or more of the monoclonal antibodies selected from the group consisting of human gastrointestinal-cell-antigen-binding monoclonal antibodies CLH6 (HB 8232), CLT85 (HB8240), CLT479 (HB8241), CLT174 (HB8242), CLH68 (HB8243), CLT152 (HB8244), CLH70 (HB8245), HT29/15 (HB8246), HT29/26 (HB8247), HT29/36 (HB8248), CLT218 (HB8249), CLT15 (HB8250), CLT307 (HB8251), and CLT86 (HB8252) and detecting the presence or absence of immune complex formation with two or more of said monoclonal antibodies indicating the presence or absence of abnormality in the gastrointestinal specimen.

10. Method of claim 9 wherein a panel of monoclonal antibodies selected from the group consisting of human gastrointestinal-cell-antigen-binding monoclonal antibodies CLH6 (HB 8232), CLT85 (HB8240), CLT479 (HB8241), CLT174 (HB8242), CLH68 (HB8243), CLT152 (HB8244), CLH70 (HB8245), HT29/15 (HB8246), HT29/26 (HB8247), HT29/36 (HB8248), CLT218 (HB8249), CLT15 (HB8250), CLT307

(HB8251), and CLT86 (HB8252) diagnostic for a gastrointestinal cancer is contacted with a human gastrointestinal specimen containing gastrointestinal cellular material.

11. Method of claim 9 wherein a panel of monoclonal antibodies diagnostic for colon cancer selected from the group of human gastrointestinal-cell-antigen-binding monoclonal antibodies CLH6 (HB 8232), CLT85 (HB8240), CLT479 (HB8241), CLT174 (HB8242), CLH68 (HB8243), CLT152 (HB8244), CLH70 (HB8245), HT29/15 (HB8246), HT29/26 (HB8247), HT29/36 (HB8248), CLT218 (HB8249), CLT15 (HB8250), CLT307 (HB8251), and CLT86 (HB8252) is contacted with a human gastrointestinal specimen wherein said speciman contains colonic material.

12. Method of claim 9 wherein a panel of monoclonal antibodies differentially diagnostic for gastrointestinal cancer selected from the group consisting of human gastrointestinal-cell-antigen-binding monoclonal antibodies CLH6 (HB 8232), CLT85 (HB8240), CLT479 (HB8241), CLT174 (HB8242), CLH68 (HB8243), CLT152 (HB8244), CLH70 (HB8245), HT29/15 (HB8246), HT29/26 (HB8247), HT29/36 (HB8248), CLT218 (HB8249), CLT15 (HB8250), CLT307 (HB8251), and CLT86 (HB8252) is contacted with a human gastrointestinal specimen containing gastrointestinal cellular material.

13. Method of claim 9 wherein said specimen is singly or serially contacted with each of the panel monoclonal antibodies.

14. Method of claim 9 wherein said specimen is contacted with combinations of the panel monoclonal antibodies.

15. Method of classifying normal or abnormal human gastrointestinal cells which comprises contacting a human gastrointestinal speciman with two or more of the monoclonal antibodies selected from the group consisting of human gastrointestinal cell-antigen-binding-monoclonal antibodies CLH6 (HB 8232), CLT85 (HB8240), CLT479 (HB8241), CLT174 (HB8242), CLH68 (HB8243), CLT152 (HB8244), CLH70 (HB8245), HT29/15 (HB8246), HT29/26 (HB8247), HT29/36 (HB8248), CLT218 (HB8249), CLT15 (HB8250), CLT307 (HB8251), and CLT86 (HB8252), singly, in combination, or serially and observing the presence of absence of immune complex formation with antigens of said gastrointestinal cells.

16. A kit for determining colon cancer comprising in package form two or more of the monoclonal antibodies selected from the group consisting of human gastrointestinal-cell-antigen-binding monoclonal antibodies CLH6 (HB8232), CLT85 (HB8240), CLT479 (HB8241), CLT174 (HB8242), CLH68 (HB8243), CLT152 (HB8244), CLH70 (HB8245), HT29/15 (HB8246), HT29/26 (HB8247), HT29/36 (HB8248), CLT218 (HB8249), CLT15 (HB8250), CLT307 (HB8251), and CLT86 (HB8252).

* * * * *